United States Patent

Ganzer et al.

[11] Patent Number: 5,840,653
[45] Date of Patent: Nov. 24, 1998

[54] SUBSTITUTED PYRAZOLYLPYRAZOLE DERIVATIVES

[75] Inventors: Michael Ganzer; Helga Franke, both of Berlin; Uwe Hartfiel, Frankfurt; Jürgen Bohner, Berlin, all of Germany

[73] Assignee: Hoechst Schering AgrEvo GmbH, Berlin, Germany

[21] Appl. No.: 868,569

[22] Filed: Jun. 4, 1997

[30] Foreign Application Priority Data

Jun. 6, 1996 [DE] Germany .................. 196 23 892.7

[51] Int. Cl.⁶ .................. A01N 43/56; C07D 403/04
[52] U.S. Cl. .................. 504/280; 548/365.4
[58] Field of Search .................. 548/365.4; 504/280, 504/281, 282

[56] References Cited

U.S. PATENT DOCUMENTS

| | | | |
|---|---|---|---|
| 3,527,602 | 9/1970 | Fox et al. | 548/365.4 |
| 3,883,549 | 5/1975 | Pearson | 548/365.4 |
| 4,803,215 | 2/1989 | Jensen-Korte et al. | 514/407 |
| 4,833,246 | 5/1989 | Adachi et al. | 544/82 |
| 5,405,829 | 4/1995 | Hartfiel et al. | 504/282 |

FOREIGN PATENT DOCUMENTS

| | | |
|---|---|---|
| WO 94/08999 | 4/1994 | European Pat. Off. . |
| WO 96/09303 | 3/1996 | European Pat. Off. . |
| 196 32 347 | 3/1996 | Germany . |

*Primary Examiner*—Deborah C. Lambkin
*Attorney, Agent, or Firm*—Frommer Lawrence & Haug LLP

[57] ABSTRACT

Novel substituted pyrazolylpyrazoles of the formula I

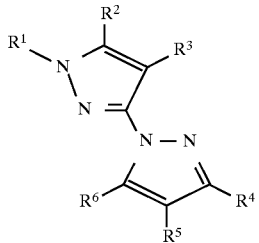

in which $R^1$–$R^6$ are as defined in the description, processes for their preparation and intermediates for their preparation and their use as herbicides are described.

5 Claims, No Drawings

SUBSTITUTED PYRAZOLYLPYRAZOLE DERIVATIVES

The invention relates to novel substituted pyrazolylpyrazoles, processes for their preparation and intermediates for their preparation, and to their use as herbicides.

It has already been disclosed that pyrazoles have herbicidal properties (WO 94/08999).

U.S. Pat. No. 5,405,829 discloses pyrazolylpyrazoles having an unsubstituted amino group as herbicidally active compounds.

WO 94/08999 describes herbicidally active pyrazolylpyrazoles, inter alia having a substituted amino group.

WO 96/09303 likewise discloses substituted pyrazolylpyrazoles having herbicidal properties.

However, the herbicidal activity of the known compounds is frequently insufficient, or else, when the herbicidal activity is appropriate, there are problems with the selectivity in major agricultural crops.

It is an object of the present invention to provide novel substituted pyrazolylpyrazoles which do not have these disadvantages and which are superior to the prior art compounds in terms of biological properties.

It has now been found that substituted pyrazolylpyrazoles of the formula I

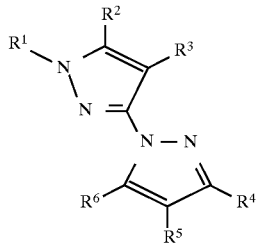

(I)

in which $R^1$ is $C_1$–$C_4$-alkyl, $R^2$ is $C_1$–$C_4$-alkyl, $C_1$–$C_4$-alkylthio, $C_1$–$C_4$-alkylsulfinyl, $C_1$–$C_4$-alkylsulfonyl, $C_1$–$C_4$-alkoxy, or is $C_1$–$C_4$-alkyl, $C_1$–$C_4$-alkylthio, $C_1$–$C_4$-alkylsulfonyl or $C_1$–$C_4$-alkoxy, each of which is mono- or polysubstituted by halogen, $R^1$ and $R^2$ together form the group —$(CH_2)_m$—, $R^3$ is hydrogen or halogen, $R^4$ is hydrogen or $C_1$–$C_4$-alkyl, $R^5$ is hydrogen, nitro, cyano, —$COOR^7$, the group

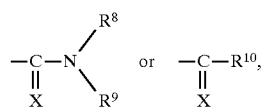

$R^6$ is one of the groups

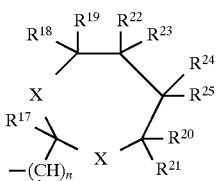

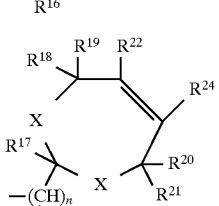

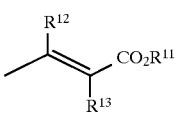

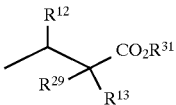

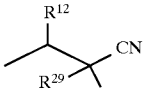

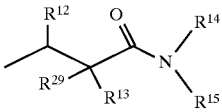

or

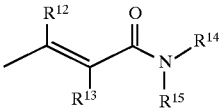

$R^7$, $R^8$ and $R^9$ independently of one another are hydrogen or $C_1$–$C_4$-alkyl, $R^8$ and $R^9$ together with the adjacent nitrogen atom form a 5- or 6-membered saturated heterocyclic ring, $R^{10}$ is hydrogen, $C_1$–$C_4$-alkyl, or $C_1$–$C_4$-alkyl which is mono- or polysubstituted by halogen, $R^{11}$ is $C_5$–$C_8$-alkyl, $C_3$–$C_6$-cycloalkyl, $C_2$–$C_6$-alkenyl, $C_3$–$C_6$-alkynyl, or is a $C_1$–$C_6$-alkyl, $C_3$–$C_6$-cycloalkyl, $C_2$–$C_6$-alkenyl or $C_3$–$C_6$-alkynyl which is mono-or polysubstituted by identical or different substituents from the group consisting of halogen, cyano, hydroxyl and $C_1$–$C_4$-alkoxy, or is a $C_2$–$C_8$-alkyl, $C_3$–$C_8$-cycloalkyl, $C_3$–$C_8$-cycloalkyl-$C_1$–$C_4$-alkyl, $C_3$–$C_8$-alkenyl or $C_3$–$C_8$-alkynyl which is interrupted once or more than once by oxygen, or is $C_1$–$C_4$-alkoxycarbonyl-$C_1$–$C_4$-alkyl which may optionally be substituted by halogen atoms, or is $C_1$–$C_4$- alkoxycarbonyl-$C_2$–$C_4$-alkenyl which is optionally substituted by halogen, or is the group —$(CH_2)_p$—$NR^8R^9$, $R^{12}$ and $R^{13}$ independently of each other are hydrogen, halogen, $C_1$–$C_4$-alkyl, $C_2$–$C_4$-alkenyl, $C_3$–$C_4$-alkynyl or $C_1$–$C_4$-alkoxy, or a $C_1$–$C_4$-alkyl, $C_2$–$C_4$-alkenyl or $C_3$–$C_4$-alkynyl which is mono- or polysubstituted by identical or different substituents from the group consisting of halogen, cyano, carboxyl, hydroxyl, $C_1$–$C_4$-alkoxy and $C_1$–$C_4$-alkoxycarbonyl, A is cyano,

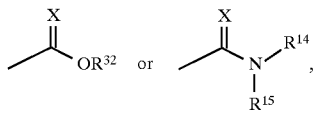

$R^{14}$ and $R^{15}$ independently of each other are hydrogen, $C_1$–$C_6$-alkyl, $C_3$–$C_6$-cycloalkyl, $C_2$–$C_6$-alkenyl or $C_3$–$C_6$-alkynyl, or a $C_1$–$C_6$-alkyl, $C_3$–$C_6$-cycloalkyl, $C_2$–$C_6$-alkenyl or $C_3$–$C_6$-alkynyl which is mono- or polysubstituted by identical or different substituents from the group consisting of halogen, cyano, hydroxyl or $C_1$–$C_4$-alkoxy, or a $C_2$–$C_8$-alkyl, $C_3$–$C_8$-cycloalkyl, $C_2$–$C_8$-alkenyl and $C_3$–$C_8$-alkynyl which is interrupted once or more than once by oxygen, or $C_1$–$C_4$-alkoxycarbonyl-$C_1$–$C_4$-alkyl which may optionally be substituted by halogen or $C_1$–$C_4$-alkoxycarbonyl-$C_2$–$C_4$-alkenyl which may optionally be substituted by halogen, or $C_1$–$C_4$-alkoxycarbonyl, $R^{14}$ and $R^{15}$ together with the nitrogen atom form a saturated heterocyclic $C_3$–$C_6$-ring which may be interrupted once or more than once by oxygen or sulfur, $R^{16}$ is hydrogen or $C_1$–$C_4$-alkyl, $R^{17}$ is hydrogen, $C_1$–$C_4$-alkyl or halo-$C_1$–$C_4$-alkyl, $R^{18}$, $R^{19}$, $R^{20}$, $R^{21}$, $R^{22}$ and $R^{24}$ independently of one another are hydrogen, halogen, $C_1$–$C_4$-alkyl, $C_2$–$C_4$-alkenyl or $C_3$–$C_4$-alkynyl, carboxyl or $C_1$–$C_4$-alkoxycarbonyl, or a $C_1$–$C_4$-alkyl, $C_2$–$C_4$-alkenyl or $C_3$–$C_4$-alkynyl which is mono- or polysubstituted by identical or different substituents from the group consisting of halogen, cyano, nitro, hydroxyl and $C_1$–$C_4$-alkoxy, $R^{23}$ and $R^{25}$ are hydrogen, halogen, $C_1$–$C_4$-alkyl, $C_2$–$C_4$-alkenyl or $C_3$–$C_4$-alkynyl, or $R^{23}$ and $R^{25}$ together form a saturated or unsaturated carbocyclic or heterocyclic three to eight membered ring optionally containing one or more than one sulfur or oxygen atoms, $R^{29}$ is hydrogen or halogen, $R^{31}$ is hydrogen, $C_1$–$C_4$-alkyl, $C_5$–$C_8$-alkyl, $C_3$–$C_6$-cycloalkyl, $C_2$–$C_6$-alkenyl, $C_3$–$C_6$-alkynyl, or is a $C_1$–$C_6$-alkyl, $C_3$–$C_6$-cycloalkyl, $C_2$–$C_6$-alkenyl or $C_3$–$C_6$-alkynyl which is mono- or polysubstituted by identical or different substituents from the group consisting of halogen, cyano, hydroxyl and $C_1$–$C_4$-alkoxy, or is a $C_2$–$C_8$-alkyl, $C_3$–$C_8$-cycloalkyl, $C_3$–$C_8$-cycloalkyl-$C_1$–$C_4$-alkyl, $C_2$–$C_8$-alkenyl or $C_3$–$C_8$-alkynyl which is interrupted once or more than once by oxygen, or is $C_1$–$C_4$-alkoxycarbonyl-$C_1$–$C_4$-alkyl which may optionally be substituted by halogen, or is $C_1$–$C_4$-alkoxycarbonyl-$C_2$–$C_4$-alkenyl which may optionally be substituted by halogen, or is the group —$(CH_2)_p$—$NR^8R^9$, with the proviso that, if $R^{12}$ and $R^{31}$ are hydrogen or $R^{12}$ is hydrogen and $R^{31}$ is $C_1$–$C_4$-alkyl, $R^{13}$ may not be hydrogen or halogen, $R^{32}$ is hydrogen, $C_1$–$C_6$-alkyl, $C_3$–$C_6$-cycloalkyl, $C_2$–$C_6$-alkenyl, $C_3$–$C_6$-alkynyl, or is a $C_1$–$C_6$-alkyl, $C_3$–$C_6$-cycloalkyl, $C_2$–$C_6$-alkenyl or $C_3$–$C_6$-alkynyl which is mono- or polysubstituted by identical or different substituents from the group consisting of halogen, cyano, hydroxyl and $C_1$–$C_4$-alkoxy, or is a $C_2$–$C_8$-alkyl, $C_3$–$C_8$-cycloalkyl, $C_2$–$C_8$-alkenyl or $C_3$–$C_8$-alkynyl which is interrupted once or more than once by oxygen, or is $C_1$–$C_4$-alkoxycarbonyl-$C_1$–$C_4$-alkyl which may optionally be substituted by halogen, or is $C_1$–$C_4$-alkoxycarbonyl-$C_2$–$C_4$-alkenyl which may optionally be substituted by halogen, m is 3 or 4, n is 0, 1, 2 or 3, o is 1, 2 or 3, p is 2, 3 or 4 and X is oxygen or sulfur, have superior herbicidal activity to the prior art compounds.

The term halogen embraces fluorine, chlorine, bromine and iodine.

The terms "alkyl", "alkenyl" and "alkynyl" embrace hydrocarbon radicals which can be branched or straight-chain.

Preference is given to those substituted pyrazolylpyrazoles of the formula I in which $R^1$ is methyl, $R^2$ is difluoromethoxy, $R^1$ and $R^2$ together form the group —$(CH_2)_4$—, $R^3$ is chlorine or bromine, $R^4$ is hydrogen, $R^5$ is nitro or cyano, $R^6$ is one of the groups

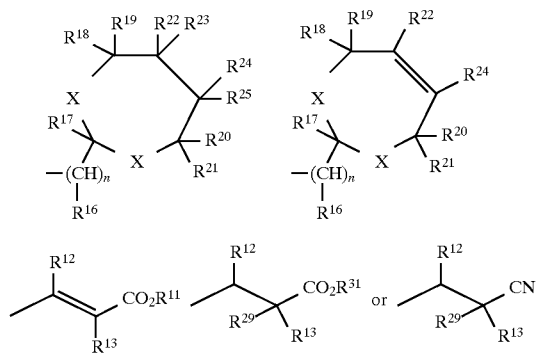

$R^{11}$ is $C_5$–$C_8$-alkyl, $C_3$–$C_6$-cycloalkyl, $C_2$–$C_6$-alkenyl, $C_3$–$C_6$-alkynyl, or is a $C_2$–$C_8$-alkyl, $C_3$–$C_8$-cycloalkyl, $C_3$–$C_8$-alkenyl or $C_3$–$C_8$-alkynyl which is interrupted once or more than once by oxygen, $R^{12}$ is hydrogen or methyl, $R^{13}$ is hydrogen or methyl, $R^{16}$ is hydrogen, $R^{17}$ is hydrogen, $R^{18}$, $R^{19}$, $R^{20}$, $R^{21}$, $R^{22}$, $R^{23}$, $R^{24}$ and $R^{25}$ independently of one another are hydrogen, halogen or $C_1$–$C_3$-alkyl, $R^{23}$ and $R^{25}$ together form a saturated 3-atom ring interrupted by an oxygen atom, $R^{29}$ is hydrogen or halogen, $R^{31}$ is hydrogen, $C_1$–$C_4$-alkyl, $C_5$–$C_8$-alkyl, $C_3$–$C_6$-cycloalkyl, $C_2$–$C_6$-alkenyl, $C_3$–$C_6$-alkynyl, or is a $C_1$–$C_6$-alkyl, $C_3$–$C_6$-cycloalkyl, $C_2$–$C_6$-alkenyl or $C_3$–$C_6$-alkynyl which is mono- or polysubstituted by identical or different substituents from the group consisting of halogen, cyano, hydroxyl and $C_1$–$C_4$-alkoxy, with the proviso that, if $R^{12}$ and $R^{31}$ are hydrogen or $R^{12}$ is hydrogen and $R^{31}$ is $C_1$–$C_4$-alkyl, $R^{13}$ may not be hydrogen, X is oxygen, and n is 0 and o is 1 or 2.

The compounds of the formula I according to the invention can be prepared by

A) reacting a compound of the formula II

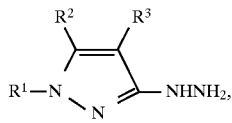

(II)

in which $R^1$, $R^2$ and $R^3$ are as defined in the formula I with a compound of the formula III

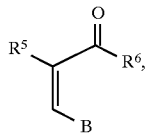

(III)

in which $R^5$ is the group $COOR^7$ or

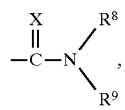

where $R^7$, $R^8$ and $R^9$ are as defined in the formula I and X is oxygen, and B is the group $OR^{26}$ or

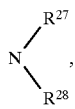

where $R^{26}$, $R^{27}$ and $R^{28}$ independently of one another are $C_1$–$C_4$-alkyl, or B) if $R^6$ is the group —$(CH_2)_o$—A, where A is the cyano group and o is as defined in the formula I, reacting a compound of the formula Ia

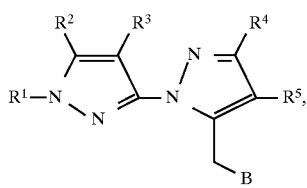

(Ia)

in which $R^1$, $R^2$, $R^3$, $R^4$ and $R^5$ are as defined in the formula I and B is a leaving group, such as chlorine, bromine or methylsulfonyl, with an alkali metal salt of hydrocyanic acid, or C) if $R^3$ is halogen, reacting a compound of the formula Ib

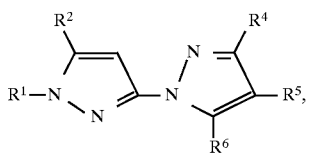

(Ib)

in which $R^1$, $R^2$, $R^4$, $R^5$ and $R^6$ are as defined in the formula I with a suitable halogenating agent, or D) if $R^6$ is one of the groups

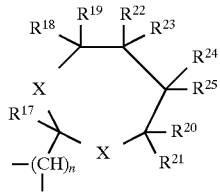

or

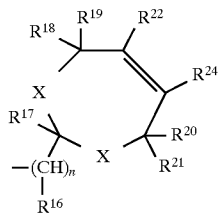

in which $R^{16}$, $R^{17}$, $R^{18}$, $R^{19}$, $R^{20}$, $R^{21}$, $R^{22}$, $R^{23}$, $R^{24}$, $R^{25}$, n and X are as defined in the formula I, reacting a compound of the formula Ic or Id,

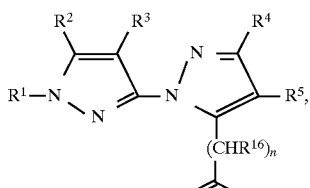

(Ic)

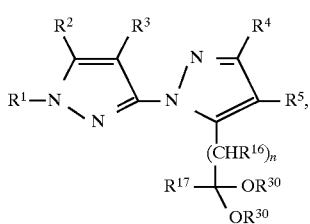

(Id)

in which $R^1$, $R^2$, $R^3$, $R^4$, $R^5$, $R^{16}$, $RK^{17}$ and n are as defiend in the formula I and $R^{30}$ is $C_1$–$C_4$-alkyl with a compound of the formula IV or V

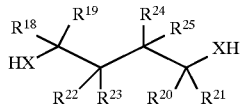

(IV)

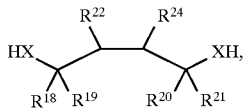

(V)

in which $R^{18}$, $R^{19}$, $R^{20}$, $R^{21}$, $R^{22}$, $R^{23}$, $R^{24}$, $R^{25}$ and X are as defined in the formula I, or E) if $R^6$ is the group

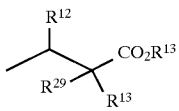

in which $R^{12}$, $R^{13}$ and $R^{31}$ are as defined in the formula I and $R^{29}$ is chlorine or bromine, first reacting, by diazotization, a compound of the formula Ie

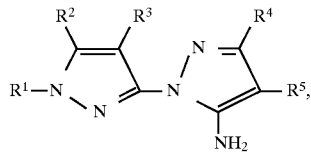

in which $R^1$, $R^2$, $R^3$, $R^4$ and $R^5$ are as defined in the formula I to give a compound of the formula If

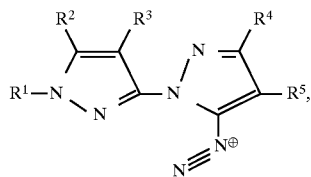

in which $R^1$, $R^2$, $R^3$, $R^4$ and $R^5$ are as defined in the formula I, and then reacting If with a Michael acceptor of the formula VI

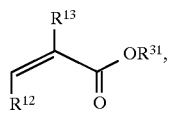

in which $R^{12}$, $R^{13}$ and $R^{31}$ are as defined in the formula I, or

F) if $R^6$ is the group

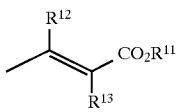

in which $R^{11}$, $R^{12}$ and $R^{13}$ are as defined in the formula I, reacting a compound of the formula Ig

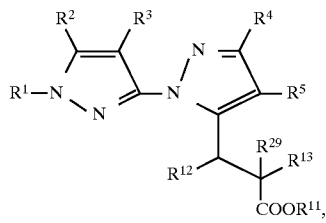

in which $R^1$, $R^2$, $R^3$, $R^4$, $R^5$, $R^{11}$, $R^{12}$ and $R^{13}$ are as defined in the formula I and $R^{29}$ is chlorine or bromine with a suitable base, or G) reacting a compound of the formula Ih or Ii

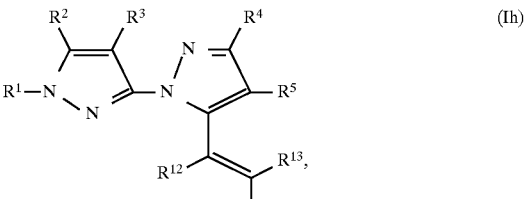

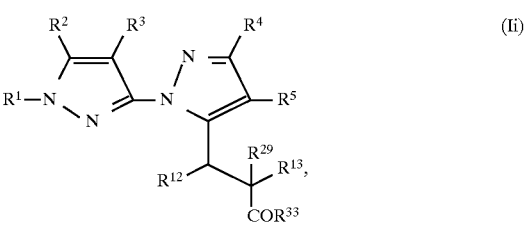

in which $R^1$, $R^2$, $R^3$, $R^4$, $R^5$, $R^{12}$, $R^{13}$ and $R^{29}$ are as defined in the formula I and $R^{33}$ is hydroxyl, chlorine, bromine or $C_1$–$C_4$-alkoxy with an alcohol of the formula VII or an amine of the formula VIII $$R^{11}\text{—OH} \qquad (VII)$$

$$R^{14}R^{15}NH \qquad (VIII)$$

in which $R^{11}$, $R^{14}$ and $R^{15}$ are as defined in the formula I.

The compounds of the formula 11 used as starting material according to process variant A are known. Their preparation is described in WO 94/08999.

The compounds of the formula I according to the invention in which $R^5$ is the group —$COOR^7$ or —$CXNR^8R^9$ (process variant A) can be prepared by the process described by Bisagni et al. in Tetrahedron 29, 435 (1973).

The process variant B) is carried out advantageously by reacting the starting material of the formula la in a suitable solvent at a temperature of 20° to 180° C. with a salt of hydrocyanic acid.

Suitable solvents are, for example, ethers, such as diethyl ether, tetrahydrofuran or 1,4-dioxane, amides, such as dimethylformamide, dimethylacetamide or N-methylpyrrolidone, aromatic hydrocarbons, such as benzene, toluene or xylene, or sulfoxides, such as dimethyl sulfoxide.

Suitable cyanides include lithium cyanide, sodium cyanide and potassium cyanide.

The compounds of the formula Ia used as starting material are known. Their preparation is described in WO 94108999.

The halogenation according to process variant C) can be carried out by processes known per se for halogenating heterocyclic aromatics, as described for example in Houben-Weyl, Volume V/4, page 233 ff (1960) or Volume V/3, page 511 ff (1962), by using a halogenating agent in a suitable inert solvent.

Suitable halogenating agents include, for example, sulfuryl chloride, sodium hypochlorite, N-chlorosuccinimide, N-bromosuccinimide, chlorine or bromine.

The acetals or ketals can be prepared according to the process variant D) by the methods described in T. W. Greene "Protective Groups in Organic Synthesis", 1980, page 116 ff.

The compounds of the formulae Ic and Id used as starting material are known. Their preparation is described in WO 94/08999.

The compounds according to process variant E) can be prepared by the process described in U.S. Pat. No. 5,250,504.

The compounds of the formula Ie used as starting material are known. Their preparation is described in WO 94/08999.

The compounds according to process variant F) can be prepared by elimination processes known per se, as described for example in J. March "Advanced Organic Chemistry" 2nd edition 1977, page 895 ff and the literature cited therein.

The esterifications according to process step G) are known per se and can be carried out by the customary methods, as described for example in Houben-Weyl, Volume E5, page 659 ff (1985). This also applies to the formation of amides, which are also described for example in Houben-Weyl, Volume E5, page 934 ff (1985).

The individual process steps can be carried out with or without solvent; if required, those solvents or diluents are used which are inert to the reactants in question. Examples of such solvents or diluents are aliphatic, alicyclic and aromatic hydrocarbons which can in each case be optionally chlorinated, for example hexane, cyclohexane, petroleum ether, ligroin, benzene, toluene, xylene, methylene chloride, chloroform, carbon tetrachloride, ethylene chloride, trichloroethylene and chlorobenzene, ethers such as, for example, diethyl ether, methyl ethyl ether, methyl t-butyl ether, diisopropyl ether, dibutyl ether, dioxane and tetrahydrofuran, ketones such as, for example, acetone, methyl ethyl ketone, methyl isopropyl ketone and methyl isobutyl ketone, nitriles such as, for example, acetonitrile and propiontrile, alcohols such as, for example, methanol, ethanol, isopropanol, butanol, tert-butanol, tert-amyl alcohol and ethylene glycol, esters such as, for example, ethyl acetate and amyl acetate, acid amides such as, for example, dimethylformamide and dimethylacetamide, sulfoxides such as, for example, dimethyl sulfoxide, and sulfones such as, for example, sulfolane, bases such as, for example, pyridine and triethylamine, carboxylic acids such as, for example, acetic acid, and mineral acids such as, for example, sulfuric acid and hydrochloric acid.

The compounds according to the invention are worked up in the customary manner. They are purified by crystallization or column chromatography.

As a rule, the compounds according to the invention are colorless or pale yellow crystalline or viscous substances, some of which are readily soluble in chlorinated hydrocarbons such as, for example, methylene chloride or chloroform, ethers such as, for example, diethyl ether or tetrahydrofuran, alcohols such as, for example, methanol or ethanol, ketones such as for example, acetone or butanone, amides such as, for example, dimethylformamide, or else sulfoxides such as, for example, dimethyl sulfoxide.

The compounds according to the invention show a good herbicidal activity on broad-leaved weeds and in grasses. Selective use is possible in a variety of crops, for example in oilseed rape, beet, soybeans, cotton, rice, maize, barley, wheat and other cereal species. Individual compounds are also suitable as selective herbicides in beet, cotton, soybeans, maize and cereals. Equally, the compounds can be employed for controlling weeds in perennial crops such as, for example, in afforestations, plantations of woody ornamentals, orchards, vineyards, citrus stands, nut orchards, banana plantations, coffee plantations, tea plantations, rubber plantations, oil palm plantations, cocoa plantations, and in soft fruit and hop fields.

The compounds according to the invention can be used for example in the following plant genera:
dicotyledonous weeds of genera such as Sinapis, Lepidium, Galium, Stellaria, Matricaria, Anthemis, Galinsoga, Chenopodium, Brassica, Urtica, Senecio, Amaranthus, Portulaca, Xanthium, Convolvulus, Ipomoea, Polygonum, Sesbaniia, Ambrosia, Cirsium, Sonchus, Solanum, Lamium, Veronica, Abutilon, Datura, Viola, Galeopsis, Papaver, Centaurea and Chrysanthemum; monocotyledonous weeds of the genera such as Avena, Alopecurus, Echinochloa, Setaria, Panicum, Digitaria, Poa, Eleusine, Brachiaria, Lolium, Bromus, Cyperus, Elymus, Sagittaria, Monochoria, Fimbristylis, Eleocharis, Ischaemum and Apera.

When applied pre-post-emergence, the rates of application vary between 0.001 and 5 kglha, depending on the type of application.

The intensity of action and speed of action can be promoted for example by activity-enhancing additives such as organic solvents, wetting agents and oils. Such additives may therefore allow a reduced dosage of active substance.

The active substances according to the invention or mixtures of these are advantageously used in the form of preparations such as powders, materials for spreading, granules, solutions, emulsions or suspensions, with an addition of liquid and/or solid carriers or diluents and, if appropriate, tackifiers, wetting agents, emulsifiers and/or dispersants.

Examples of suitable liquid carriers are aliphatic and aromatic hydrocarbons such as benzene, toluene, xylene, cyclohexanone, isophorone, dimethyl sulfoxide, dimethylformamide, and furthermore mineral oil fractions and vegetable oils.

Suitable solid carriers are minerals such as, for example, bentonite, silica gel, talc, kaolin, attapulgite, limestone and products of vegetable origin, such as, for example, meals.

Surfactants which may be mentioned are, for example, calcium lignosulfonate, polyethlene alkylphenyl ethers, naphthalenesulfonic acids and their salts, phenolsulfonic acids and their salts, formaldehyde condensates, fatty alcohol sulfates, and also substituted benzenesulfonic acids and their salts.

The amount of active substance(s) in the various products can vary within wide limits. For example, the compositions comprise approximately 10 to 90% by weight of active ingredient, approximately 90 to 10% by weight of liquid or solid carriers and, if appropriate, up to 20% by weight of surfactants.

The compositions can be applied in the customary manner, for example using water as the carrier in amounts of spray mixture of approximately 100 to 1000 liters/ha. Application of the compositions by the low-volume and ultra-low volume method is also possible, as is their application in the form of microgranules.

These products can be prepared in a manner known per se, for example by grinding or mixing processes. If desired, products comprising the individual components may also be mixed only shortly prior to use as is the case, for example, under practice conditions when using the tank mix method.

The examples below illustrate the preparation of the compounds according to the invention.

EXAMPLE 1

(Process D)

1-(4-Bromo-5-difluoromethoxy-1-methyl-3-pyrazolyl)-5-(4,7-dihydro-1,3-dioxepin-2-yl)-1H-pyrazole4-carbonitrile 3.0 g (7.1 mmol) of 1-(4-bromo-5-difluoromethoxy-1-methyl-3-pyrazolyl)-5-(1,1-diethoxyethyl)-1H-pyrazole-4-carbonitrile are dissolved in 50 ml of toluene, and 6.3 g (71 mmol) of cis-2,3-butene-1,4-diol and a catalytic amount of p-toluenesulfonic acid are then added. The mixture is kept at the boil for half an hour under a water separator, and the cooled solution is washed with sodium chloride solution, dried with magnesium sulfate and concentrated. The residue is purified by column chromatography.
Yield: 2.5 g ≙ 83% of theory, Mp.: 90°–91° C.

EXAMPLE 2

(Process E)

Methyl 1-(4-chloro-5-difluoromethoxy-1-methyl-3-pyrazolyl)-4-cyano-5-pyrazolyl-3-(2-chloro-2-methyl)propionate 1.5 g (13 mmol) of tert-butyl nitrite, 15 ml of methyl methacrylate and 1.0 g of copper(II) chloride are initially charged in 15 ml of acetonitrile, and 2.55 g (10 mmol) of 5-amino-1-(4-chloro-5-difluoromethoxy-1-methyl-3-pyrazolyl)-4-pyrazolecarbonitrile are added in 3 portions. The mixture is stirred at room temperature for 2 hours, poured into 50 ml of 2N hydrochloric acid and this mixture is extracted three times with dichloromethane, and the extract is dried over magnesium sulfate and concentrated. The product is purified by column chromatography with hexane/ethyl acetate mixtures.
Yield: 1.65 g=46% of theory, Mp.: 65° C.

EXAMPLE 3

(Process F)

Methyl 1-(4-chloro-5-difluoromethoxy-1-methyl-3-pyrazolyl)-4-cyano-5-pyrazolyl-3-(2-methyl)prop-2-enoate 73 mg (2.45 mmol) of sodium hydride (80% strength) are initially charged in 20 ml of absolute dimethylformamide, and 1.0 g (2.45 mmol) of methyl 1-(4-chloro-5-difluoromethoxy-1-methyl-3-pyrazolyl)-4-cyano-5-pyrazolyl-3-(2-chloro-2-methyl)propionate are added. The mixture is stirred at 60° C. for 2 hours, the solvent is removed under reduced pressure and the residue is purified by column chromatography using a hexane/ethyl acetate mixture.
Yield: 0.56 g=61% of theory, Mp.: 88° C.

EXAMPLE 4

(Process G)

2,2-Dimethoxyethyl (E)-3-[1-(4-chloro-5-difluoromethoxy-1-methyl-3-pyrazolyl)-4-cyano-5-pyrazolyl]acrylate 1 g (2.76 mmol) of 1-(4-chloro-5-difluoromethoxy-1-methyl-3-pyrazolyl)-4-cyano-5-pyrazolyl-3-propionyl chloride are initially charged in 20 ml of dichloromethane, and 0.28 g (2.76 mmol) of triethylamine and 0.29 g (2.76 mmol) of glycolaldehyde dimethyl acetal are added at room temperature. The mixture is stirred at room temperature for 2 hours, the solvent is removed under reduced pressure and the residue is purified by column chromatography using hexane/ethyl acetate mixtures.
Yield: 0.80 g ≙ 67% of theory, Mp.: 92° C.

The following compounds of the formula I according to the invention where $R^4$ is hydrogen and "t" above a double bond means the trans-configuration of this double bond are prepared in a similar manner:

TABLE

| No. | $R^1$ | $R^2$ | $R^3$ | $R^5$ | $R^6$ | Mp. [°C.] or $n_D$*C |
|---|---|---|---|---|---|---|
| 5 | $CH_3$ | $OCHF_2$ | Cl | CN | (structure) | 120–121 |
| 6 | $CH_3$ | $OCHF_2$ | Br | CN | (structure) | 141–142 |
| 7 | $CH_3$ | $OCHF_2$ | Cl | CN | (structure) | |
| 8 | $CH_3$ | $OCHF_2$ | Cl | CN | (structure) | |

TABLE-continued
| No. | R¹ | R² | R³ | R⁵ | R⁶ | Mp. [°C.] or $n_D^{*C}$ |
|---|---|---|---|---|---|---|
| 9 | CH₃ | OCHF₂ | Cl | CN | 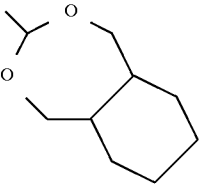 | viscous oil |
| 10 | CH₃ | OCHF₂ | Br | CN | 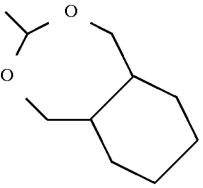 | viscous oil |
| 11 | CH₃ | OCHF₂ | Br | CN | 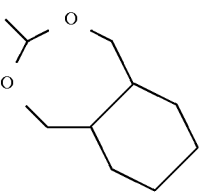 | viscous oil |
| 12 | CH₃ | OCHF₂ | Cl | CN | 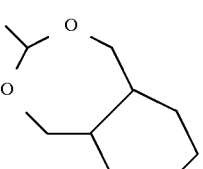 | viscous oil |
| 13 | CH₃ | OCHF₂ | Cl | CN | 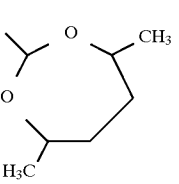 | |
| 14 | CH₃ | OCHF₂ | Br | CN | 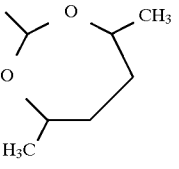 | |
| 15 | CH₃ | OCHF₂ | Cl | CN |  | 58–60 |
| 16 | CH₃ | OCHF₂ | Br | CN | 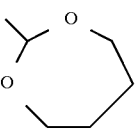 | viscous oil |
| 17 | CH₃ | OCHF₂ | Cl | CN | 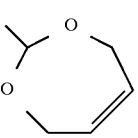 | 58–60 |

TABLE-continued
| No. | R¹ | R² | R³ | R⁵ | R⁶ | Mp. [°C.] or $n_D*C$ |
|---|---|---|---|---|---|---|
| 18 | —(CH₂)₄— | | Cl | CN | 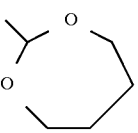 | |
| 19 | —(CH₂)₄— | | Cl | CN | 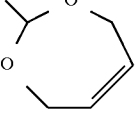 | |
| 20 | —(CH₂)₄— | | Br | CN | 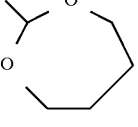 | |
| 21 | —(CH₂)₄— | | Br | CN | 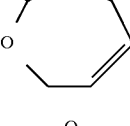 | |
| 22 | —(CH₂)₄— | | Cl | NO₂ | 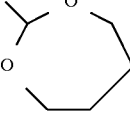 | |
| 23 | —(CH₂)₄— | | Cl | NO₂ | 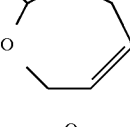 | |
| 24 | —(CH₂)₄— | | Br | NO₂ | 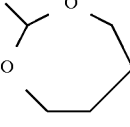 | |
| 25 | —(CH₂)₄— | | Br | NO₂ | 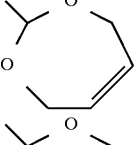 | |
| 26 | CH₃ | OCHF₂ | Cl | NO₂ | 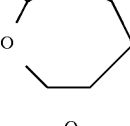 | |
| 27 | CH₃ | OCHF₂ | Br | NO₂ | 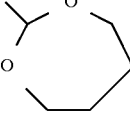 | |
| 28 | CH₃ | OCHF₂ | Cl | NO₂ | 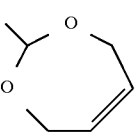 | |

TABLE-continued

| No. | R¹ | R² | R³ | R⁵ | R⁶ | Mp. [°C.] or $n_D$ *C |
|---|---|---|---|---|---|---|
| 29 | CH₃ | OCHF₂ | Br | NO₂ | 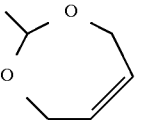 | |
| 30 | CH₃ | OCHF₂ | Br | CN | —CH₂—CN | |
| 31 | CH₃ | OCHF₂ | Cl | NO₂ | —CH₂—CN | |
| 32 | CH₃ | OCHF₂ | Cl | CN | —CH₂—CN | |
| 33 | CH₃ | OCHF₂ | Cl | CN | 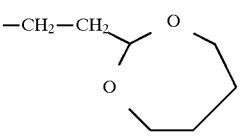 | |
| 34 | CH₃ | OCHF₂ | Cl | CN | —CH=$^t$CH—CO₂C₅H₁₁ | |
| 35 | CH₃ | OCHF₂ | Cl | CN | —CH=$^t$CH—CONH₂ | 190–192 |
| 36 | —(CH₂)₄— | | Cl | CN | —CH=$^t$CH—CONH₂ | |
| 37 | —(CH₂)₄— | | Cl | CN | —CH=$^t$CH—CO₂C₅H₁₁ | |
| 38 | CH₃ | OCHF₂ | Cl | CN | —CH=$^t$CH—CONH(CH₃) | 52–54 |
| 39 | —(CH₂)₄— | | Cl | CN | —CH=$^t$CH—CONH(CH₃)₂ | |
| 40 | CH₃ | OCHF₂ | Cl | CN | —CH=$^t$CH—CONH(C₃H₇) | |
| 41 | —(CH₂)₄— | | Cl | CN | —CH=$^t$CH—CON(C₂H₅)₂ | |
| 42 | CH₃ | OCHF₂ | Cl | CN | 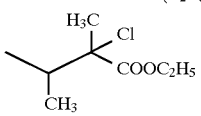 | |
| 43 | —(CH₂)₄— | | Cl | CN | 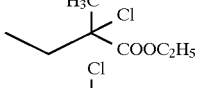 | |
| 44 | CH₃ | OCHF₂ | Cl | CN | 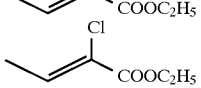 | |
| 45 | —(CH₂)₄— | | Cl | CN | 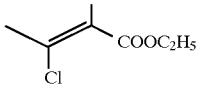 | |
| 46 | CH₃ | OCHF₂ | Cl | CN | 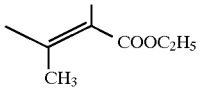 | |
| 47 | —(CH₂)₄— | | Cl | CN | 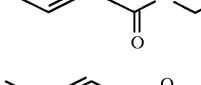 | |
| 48 | CH₃ | OCHF₂ | Cl | CN | 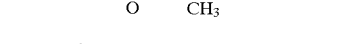 | 116 |
| 49 | CH₃ | OCHF₂ | Cl | CN |  | |
| 50 | CH₃ | OCHF₂ | Cl | CN | 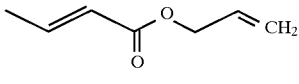 | |
| 51 | CH₃ | OCHF₂ | Cl | CN |  | 110 |

TABLE-continued
| No. | R¹ | R² | R³ | R⁵ | R⁶ | Mp. [°C.] or $n_D^{*C}$ |
|---|---|---|---|---|---|---|
| 52 | CH₃ | OCHF₂ | Cl | CN | 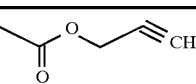 | 112 |
| 53 | CH₃ | OCHF₂ | Cl | CN | 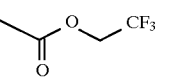 | 91–92 |
| 54 | CH₃ | OCHF₂ | Cl | CN | 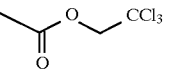 | 107–108 |
| 55 | CH₃ | OCHF₂ | Cl | CN | 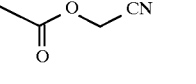 | |
| 56 | CH₃ | OCHF₂ | Cl | CN | 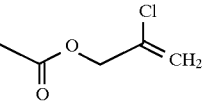 | |
| 57 | CH₃ | OCHF₂ | Cl | CN | 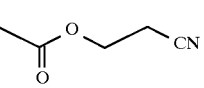 | |
| 58 | CH₃ | OCHF₂ | Cl | CN | 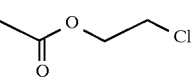 | |
| 59 | CH₃ | OCHF₂ | Cl | CN | 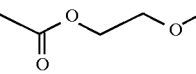 | |
| 60 | CH₃ | OCHF₂ | Cl | CN | 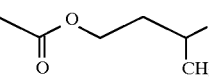 | |
| 61 | CH₃ | OCHF₂ | Cl | CN | 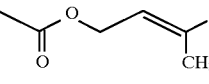 | |
| 62 | CH₃ | OCHF₂ | Cl | CN | 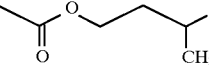 | |
| 63 | CH₃ | OCHF₂ | Cl | CN | 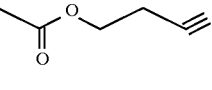 | |
| 64 | CH₃ | OCHF₂ | Cl | CN | 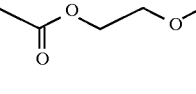 | |
| 65 | CH₃ | OCHF₂ | Br | CN | 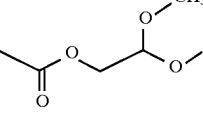 | |
| 66 | CH₃ | OCHF₂ | Cl | CN | 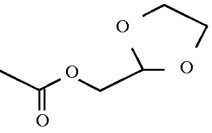 | |
| 67 | CH₃ | OCHF₂ | Cl | CN | 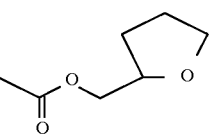 | |

TABLE-continued

| No. | R¹ | R² | R³ | R⁵ | R⁶ | Mp. [°C.] or $n_D^{*C}$ |
|---|---|---|---|---|---|---|
| 68 | $CH_3$ | $OCHF_2$ | Cl | CN | crotonate ester of 2,2-dimethyl-1,3-dioxolan-4-yl methanol | |
| 69 | $CH_3$ | $OCHF_2$ | Cl | CN | crotonate ester of (1,3-dioxan-2-yl)methanol | |
| 70 | $CH_3$ | $OCHF_2$ | Cl | CN | α-chloro-crotonate ester of (1,3-dioxan-2-yl)methanol | |
| 71 | $CH_3$ | $OCHF_2$ | Br | CN | crotonate ester of (1,3-dioxolan-2-yl)methanol | |
| 72 | $CH_3$ | $OCHF_2$ | Cl | CN | 2-(dimethylamino)ethyl crotonate | |
| 73 | $CH_3$ | $OCHF_2$ | Cl | CN | 2-(piperidin-1-yl)ethyl crotonate | |
| 74 | $CH_3$ | $OCHF_2$ | Cl | CN | oxetan-3-yl crotonate | |
| 75 | $CH_3$ | $OCHF_2$ | Cl | CN | $-CH\overset{t}{=}CH-CO_2CH_2CO_2CH_3$ | 114 |
| 76 | $CH_3$ | $OCHF_2$ | Cl | CN | 1-(piperidin-1-yl)but-2-en-1-one | |
| 77 | $CH_3$ | $OCHF_2$ | Cl | CN | N,N-diethyl crotonamide | 76–78 |
| 78 | $CH_3$ | $OCHF_2$ | Cl | CN | N-methoxy-N-methyl crotonamide | |
| 79 | $CH_3$ | $OCHF_2$ | Cl | CN | 1-(pyrrolidin-1-yl)but-2-en-1-one | |

TABLE-continued

| No. | R¹ | R² | R³ | R⁵ | R⁶ | Mp. [°C.] or $n_D$ *C |
|---|---|---|---|---|---|---|
| 80 | CH₃ | OCHF₂ | Cl | CN | (E)-CH₃-CH=CH-C(O)-N(morpholino) | |
| 81 | CH₃ | OCHF₂ | Cl | CN | (E)-CH₃-CH=CH-C(O)-N(CH₃)(CH₂CH₂OMe) | |
| 82 | CH₃ | OCHF₂ | Br | CN | —CH₂—CONH₂ | |
| 83 | CH₃ | OCHF₂ | Cl | NO₂ | —CH₂—CONH₂ | |
| 84 | CH₃ | OCHF₂ | Cl | CN | —CH₂—CONH₂ | |
| 85 | CH₃ | OCHF₂ | Br | CN | —CH₂—COOC₂H₅ | |
| 86 | CH₃ | OCHF₂ | Cl | NO₂ | —CH₂—COOC₂H₅ | |
| 87 | CH₃ | OCHF₂ | Cl | CN | —CH₂—COOC₂H₅ | |
| 88 | CH₃ | OCHF₂ | Cl | CN | CH₃(CH₂)₃C(O)O-CH₂-CH(-O-CH₂CH₂CH₂-O-) (1,3-dioxane) | |
| 89 | —(CH₂)₄— | | Cl | CN | CH₃(CH₂)₃C(O)OCH₂CH₃ | |
| 90 | —(CH₂)₄— | | Cl | CN | (E)-CH₃-CH=CH-C(O)-O-CH₂CH₂-OCH₃ | |
| 91 | —(CH₂)₄— | | Cl | CN | (E)-CH₃-CH=CH-C(O)-O-CH(CH₃)-CH₂-O-C₂H₅ | |
| 92 | —(CH₂)₄— | | Cl | CN | (E)-CH₃-CH=CH-C(O)-O-CH₂-CH=CH-CH₃ | |
| 93 | —(CH₂)₄— | | Cl | CN | (E)-CH₃-CH=CH-C(O)-O-CH₂-CH=CH₂ | |
| 94 | —(CH₂)₄— | | Cl | CN | (E)-CH₃-CH=CH-C(O)-O-CH₂-C≡CH | |
| 95 | —(CH₂)₄— | | Cl | CN | (E)-CH₃-CH=CH-C(O)-O-CH₂-CF₃ | |
| 96 | —(CH₂)₄— | | Cl | CN | (E)-CH₃-CH=CH-C(O)-O-CH₂-CCl₃ | |
| 97 | —(CH₂)₄— | | Cl | CN | (E)-CH₃-CH=CH-C(O)-O-CH₂-CN | |
| 98 | —(CH₂)₄— | | Cl | CN | (E)-CH₃-CH=CH-C(O)-O-CH₂-C(Cl)=CH₂ | |
| 99 | —(CH₂)₄— | | Cl | CN | (E)-CH₃-CH=CH-C(O)-O-CH₂CH₂-CN | |

TABLE-continued

| No. | R¹ | R² | R³ | R⁵ | R⁶ | Mp. [°C.] or $n_D$*C |
|---|---|---|---|---|---|---|
| 100 | —(CH₂)₄— | | Cl | CN | CH=CH-C(=O)-O-CH₂-CH₂-Cl | |
| 101 | —(CH₂)₄— | | Cl | CN | CH=CH-C(=O)-O-CH₂-CH₂-O-CH₃ | |
| 102 | —(CH₂)₄— | | Cl | CN | CH=CH-C(=O)-O-CH₂-CH(CH₃)₂ | |
| 103 | —(CH₂)₄— | | Cl | CN | CH=CH-C(=O)-O-CH₂-CH=C(CH₃)₂ | |
| 104 | —(CH₂)₄— | | Cl | CN | CH=CH-C(=O)-O-CH₂-C(OMe)=CH(CH₃) | |
| 105 | —(CH₂)₄— | | Cl | CN | CH=CH-C(=O)-O-CH₂-CH₂-C≡CH | |
| 106 | —(CH₂)₄— | | Cl | CN | CH=CH-C(=O)-O-CH₂-CH₂-O-CH₂-CH₂-O-CH₃ | |
| 107 | —(CH₂)₄— | | Cl | CN | CH=CH-C(=O)-O-CH₂-CH(OCH₃)₂ | |
| 108 | —(CH₂)₄— | | Cl | CN | CH=CH-C(=O)-O-CH₂-(1,3-dioxolan-2-yl) | |
| 109 | —(CH₂)₄— | | Cl | CN | CH=CH-C(=O)-O-CH₂-(tetrahydrofuran-2-yl) | |
| 110 | —(CH₂)₄— | | Cl | CN | CH=CH-C(=O)-O-CH₂-CH(O-)-CH₂-O-C(CH₃)₂ (2,2-dimethyl-1,3-dioxolane) | |
| 111 | —(CH₂)₄— | | Cl | CN | CH=CH-C(=O)-O-CH₂-(1,3-dioxan-2-yl) | |
| 112 | —(CH₂)₄— | | Cl | CN | CCl=CH-C(=O)-O-CH₂-(1,3-dioxan-2-yl) | |

TABLE-continued

| No. | R$^1$ R$^2$ | R$^3$ | R$^5$ | R$^6$ | Mp. [°C.] or n$_D$*C |
|---|---|---|---|---|---|
| 113 | —(CH$_2$)$_4$— | Br | CN | crotonate ester of 1,3-dioxolan-2-ylmethanol | |
| 114 | —(CH$_2$)$_4$— | Cl | CN | 2-(dimethylamino)ethyl crotonate | |
| 115 | —(CH$_2$)$_4$— | Cl | CN | 2-(piperidin-1-yl)ethyl crotonate | |
| 116 | —(CH$_2$)$_4$— | Cl | CN | oxetan-3-yl crotonate | |
| 117 | —(CH$_2$)$_4$— | Cl | CN | —CH=$^t$CH—CO$_2$CH$_2$CO$_2$CH$_3$ | |
| 118 | —(CH$_2$)$_4$— | Cl | CN | 1-(piperidin-1-yl)but-2-en-1-one | |
| 119 | —(CH$_2$)$_4$— | Cl | CN | N,N-diethylcrotonamide | |
| 120 | —(CH$_2$)$_4$— | Cl | CN | N-methoxy-N-methylcrotonamide | |
| 121 | —(CH$_2$)$_4$— | Cl | CN | 1-(pyrrolidin-1-yl)but-2-en-1-one | |
| 122 | —(CH$_2$)$_4$— | Cl | CN | 1-(morpholin-4-yl)but-2-en-1-one | |
| 123 | —(CH$_2$)$_4$— | Cl | CN | N-(2-methoxyethyl)-N-methylcrotonamide | |
| 124 | —(CH$_2$)$_4$— | Br | CN | —CH$_2$—CONH$_2$ | |
| 125 | —(CH$_2$)$_4$— | Cl | NO$_2$ | —CH$_2$—CONH$_2$ | |
| 126 | —(CH$_2$)$_4$— | Cl | CN | —CH$_2$—CONH$_2$ | |
| 127 | —(CH$_2$)$_4$— | Br | CN | —CH$_2$—COOC$_2$H$_5$ | |
| 128 | —(CH$_2$)$_4$— | Cl | NO$_2$ | —CH$_2$—COOC$_2$H$_5$ | |
| 129 | —(CH$_2$)$_4$— | Cl | CN | —CH$_2$—COOC$_2$H$_5$ | |

TABLE-continued

| No. | R¹ | R² | R³ | R⁵ | R⁶ | Mp. [°C.] or $n_D$ *°C |
|---|---|---|---|---|---|---|
| 130 | —(CH$_2$)$_4$— | | Cl | CN | (pentyl ester with dioxane substituent) | |
| 131 | —(CH$_2$)$_4$— | | Cl | CN | (pentanoate ethoxymethyl ester) | |
| 132 | CH$_3$ | CF$_3$ | Cl | CN | (1,3-dioxepane) | 114 |
| 133 | CH$_3$ | CF$_3$ | Cl | CN | (1,3-dithiepane) | 109–112 |
| 134 | CH$_3$ | OCHF$_2$ | Cl | CN | —CH$\overset{t}{=}$CHCONHC$_2$H$_5$ | 48–50 |
| 135 | CH$_3$ | OCHF$_2$ | Cl | CN | —CH=CHCONHCH(CH$_3$)$_2$ | 48–50 |
| 136 | CH$_3$ | OCHF$_2$ | Cl | CN | —CH=CHCONHCH(CH$_3$)C$_2$H$_5$ | viscous oil |
| 137 | CH$_3$ | OCHF$_2$ | Cl | CN | —CH=CHCONHCH$_2$CH(CH$_3$)$_2$ | viscous oil |
| 138 | CH$_3$ | OCHF$_2$ | Cl | CN | —CH=CHCONHCH$_2$C≡CH | viscous oil |
| 139 | CH$_3$ | OCHF$_2$ | Cl | CN | —CH=CHCON(CH$_3$)$_2$ | 121–123 |
| 140 | CH$_3$ | OCHF$_2$ | Cl | CN | —CH=CHCON(CH$_3$)CH$_2$C≡CH | 93–95 |
| 141 | CH$_3$ | OCHF$_2$ | Cl | CN | —CH=CHCOOCH(CH$_3$)C≡CH | 112–114 |
| 142 | CH$_3$ | OCHF$_2$ | Cl | CN | —CH=CHCOOCH$_2$—(cyclopropyl) | 81–83 |
| 143 | CH$_3$ | OCHF$_2$ | Cl | CN | —CH=CHCOOCH$_2$—(oxiranyl) | 80–82 |
| 144 | CH$_3$ | OCHF$_2$ | Cl | CN | —CH=CHCOO—(tetrahydrofuranyl) | 103–105 |

The use examples below illustrate the invention:
Use Examples:

| Abbreviations | |
|---|---|
| ALOMY | Alopecurus myosuroides |
| AGRRE | Elymus repens |
| AVEFA | Avena fatua |
| SETVI | Setaria viridis |
| PANSS | Panicum sp. |
| SORHA | Sorghum halepense |
| ECHCG | Echinochloa crus-galli |
| DIGSA | Digitaria sanguinalis |
| POAAN | Poa annua |
| LOLMU | Lolium multiflorum |
| ABUTH | Abutilon theophrasti |
| GALAP | Galium aparine |
| PHBPU | Pharbitis purpureum |
| MATCH | Matricaria chamomilla |
| POLPE | Polygonum sp. |
| VERPE | Veronica persica |
| CHEAL | Chenopodium album |
| AMARE | Amaranthus retroflexus |
| STEME | Stellaria media |

0=no damage

1=1–24% damage

2=25–74% damage

3=75–89% damage

4=90–100% damage

The plant species given were treated post-emergence in the greenhouse with the given compounds at a rate of application of 0.03 kg of active compound/ha. To this end, the compounds were sprayed uniformly over the plants in the form of an emulsion with 500 liters of water/ha. 2 weeks after the treatment, the compounds according to the invention showed outstanding activity against the weed, as can be seen from the table below.

| Compound Example No. | ALOMYE | AGRRE | AVEFA | SETVIS | PANSSS | SORHHA | ECHCSGN | DIGSAN | POALAN | LOLMUU | ABUTHP | GALBPUH | PHATPCHE | MALPPCE | POCPEL | VEPALE | CHEAARLE | AMARME | STEME |
|---|---|---|---|---|---|---|---|---|---|---|---|---|---|---|---|---|---|---|---|
| 1  | 3 | 1 | 2 | 3 | 4 | 2 | 3 | 3 | 3 | 3 | 4 | 4 | 4 | 4 | 4 | 4 | 4 | 4 | 4 |
| 15 | 3 | 3 | 2 | 3 | 4 | 3 | 4 | 4 | 3 | 3 | 4 | 4 | 4 | 4 | 4 | 4 | 4 | 4 | 4 |
| 16 | 3 | 2 | 2 | 3 | 4 | 3 | 4 | 4 | 3 | 3 | 4 | 4 | 4 | 4 | 4 | 4 | 4 | 4 | 4 |
| 17 | 3 | 2 | 2 | 3 | 4 | 2 | 4 | 3 | 3 | 3 | 4 | 4 | 4 | 4 | 4 | 4 | 4 | 4 | 4 |
| 48 | 0 | 0 | 2 | 2 | 3 | 3 | 1 | 3 | 1 | 0 | 4 | 4 | 4 | 3 | 4 | 4 | 4 | 4 | 4 |
| 53 | 0 | 0 | 1 | 3 | 3 | 3 | 2 | 0 | 0 | 0 | 4 | 2 | 3 | 4 | 4 | 4 | 4 | 4 | 4 |
| 54 | 0 | 1 | 2 | 3 | 2 | 3 | 2 | 0 | 0 | 0 | 4 | 3 | 4 | 3 | 4 | 4 | 4 | 4 | 4 |
| 75 | 0 | 1 | 1 | 3 | 2 | 3 | 2 | 1 | 1 | 0 | 4 | 3 | 4 | 4 | 4 | 4 | 4 | 4 | 4 |
| untreated | 0 | 0 | 0 | 0 | 0 | 0 | 0 | 0 | 0 | 0 | 0 | 0 | 0 | 0 | 0 | 0 | 0 | 0 | 0 |

We claim:

1. Substituted pyrazolylpyrazoles of the formula 1

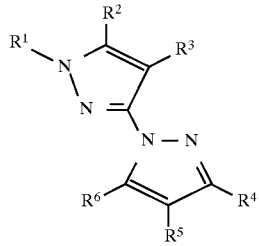

(I)

in which $R^1$ is $C_1$–$C_4$-alkyl, $R^1$ is $C_1$–$C_4$-alkyl, $C_1$–$C_4$-alkylthio, $C_1$–$C_4$-alkylsulfinyl, $C_1$–$C_4$-alkylsulfonyl, $C_1$–$C_4$-alkoxy, or is $C_1$–$C_4$-alkyl, $C_1$–$C_4$-alkylthio, $C_1$–$C_4$-alkylsulfonyl or $C_1$–$C_4$-alkoxy, each of which is mono- or polysubstituted by halogen, $R^1$ and $R^2$ together form the group —$(CH_2)_m$—, $R^3$ is hydrogen or halogen, $R^4$ is hydrogen or $C_1$–$C_4$-alkyl, $R^5$ is hydrogen, nitro, cyano, —$COOR^7$, the group

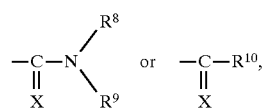

$R^6$ is one of the groups

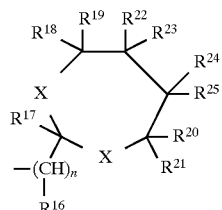

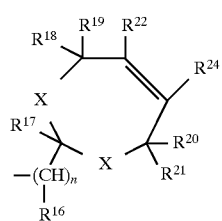

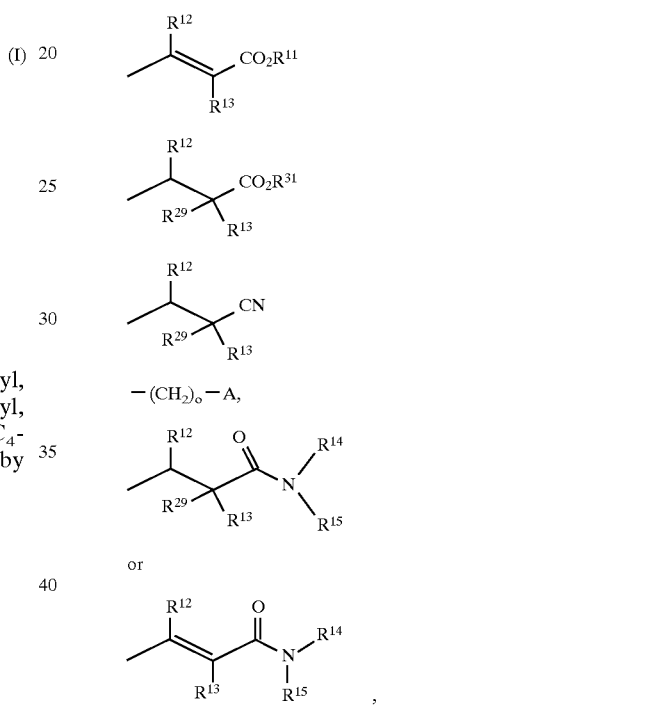

$R^7$, $R^8$ and $R^9$ independently of each other are hydrogen or $C_1$–$C_4$-alkyl, $R^8$ and $R^9$ together with the adjacent nitrogen atom form a 5- or 6-membered saturated heterocyclic ring, $R^{10}$ is hydrogen, $C_1$–$C_4$-alkyl, or $C_1$–$C_4$-alkyl which is mono- or polysubstituted by halogen, $R^{11}$ $C_5$–$C_8$-alkyl, $C_3$–$C_6$-cycloalkyl, $C_2$–$C_6$-alkenyl, $C_3$–$C_6$-alkynyl, or is a $C_1$–$C_6$-alkyl, $C_3$–$C_6$-cycloalkyl, $C_2$–$C_6$-alkenyl or $C_3$–$C_6$-alkynyl which is mono- or polysubstituted by identical or different substituents from the group consisting of halogen, cyano, hydroxyl and $C_1$–$C_4$-alkoxy, or is a $C_2$–$C_8$-alkyl, $C_3$–$C_8$-cycloalkyl, $C_3$–$C_8$-cycloalkyl-$C_1$–$C_4$-alkyl, $C_3$–$C_8$-alkenyl or $C_3$–$C_8$-alkynyl which is interrupted once or more than once by oxygen, or is $C_1$–$C_4$-alkoxycarbonyl-$C_1$–$C_4$-alkyl which may optionally be substituted by halogen atoms, or is $C_1$–$C_4$-alkoxycarbonyl-$C_2$–$C_4$-alkenyl which is optionally substituted by halogen, or is the group —$(CH_2)_p$—$NR^8R^9$, $R^{12}$ and $R^{13}$ independently of each other are hydrogen, halogen, $C_1$–$C_4$-alkyl, $C_2$–$C_4$-alkenyl, $C_3$–$C_4$-alkynyl or $C_1$–$C_4$-alkoxy, or a $C_1$–$C_4$-alkyl, $C_2$–$C_4$-alkenyl or $C_3$–$C_4$-alkynyl which is mono- or polysubstituted by identical or different substituents from the group consisting of halogen, cyano, carboxyl, hydroxyl, $C_1$–$C_4$-alkoxy and $C_1$–$C_4$-alkoxycarbonyl, A is cyano,

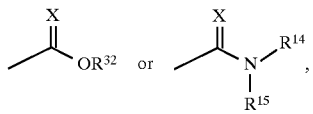

$R^{14}$ and $R^{15}$ independently of each other are hydrogen, $C_1$–$C_6$-alkyl, $C_3$–$C_6$-cycloalkyl, $C_2$–$C_6$-alkenyl or $C_3$–$C_6$-alkynyl, or a $C_1$–$C_6$-alkyl, $C_3$–$C_6$-cycloalkyl, $C_2$–$C_6$-alkenyl or $C_3$–$C_6$-alkynyl which is mono- or polysubstituted by identical or different substituents from the group consisting of halogen, cyano, hydroxyl and $C_1$–$C_4$-alkoxy, or a $C_2$–$C_8$-alkyl, $C_3$–$C_8$-cycloalkyl, $C_2$–$C_8$-alkenyl or $C_3$–$C_8$-alkynyl which is interrupted once or more than once by oxygen, or $C_1$–$C_4$-alkoxycarbonyl-$C_1$–$C_4$-alkyl which may optionally be substituted by halogen or $C_1$–$C_4$-alkoxycarbonyl-$C_2$–$C_4$-alkenyl which may optionally be substituted by halogen, or $C_1$–$C_4$-alkoxycarbonyl, $R^{14}$ and $R^{15}$ together with the nitrogen atom form a saturated heterocyclic $C_3$–$C_6$-ring which may be interrupted once or more than once by oxygen or sulfur, $R^{16}$ is hydrogen or $C_1$–$C_4$-alkyl, $R^{17}$ is hydrogen, $C_1$–$C_4$-alkyl or halo-$C_1$–$C_4$-alkyl, $R^{18}$, $R^{19}$, $R^{20}$, $R^{21}$, $R^{22}$ and $R^{24}$ independently of each other are hydrogen, halogen, $C_1$–$C_4$-alkyl, $C_2$–$C_4$-alkenyl or $C_3$–$C_4$-alkynyl, carboxyl or $C_1$–$C_4$-alkoxycarbonyl, or a $C_1$–$C_4$-alkyl, $C_2$–$C_4$-alkenyl or $C_3$–$C_4$-alkynyl which is mono- or polysubstituted by identical or different substituents from the group consisting of halogen, cyano, nitro, hydroxyl and $C_1$–$C_4$-alkoxy, $R^{23}$ and $R^{25}$ are hydrogen, halogen, $C_1$–$C_4$-alkyl, $C_2$–$C_4$-alkenyl or $C_3$–$C_4$-alkynyl, or $R^{23}$ and $R^{25}$ together form a saturated or unsaturated carbocyclic or heterocyclic three to eight membered ring optionally containing one or more than one sulfur or oxygen atoms, $R^{29}$ is hydrogen or halogen, $R^{31}$ is hydrogen, $C_1$–$C_4$-alkyl, $C_5$–$C_8$-alkyl, $C_3$–$C_6$-cycloalkyl, $C_2$–$C_6$-alkenyl, $C_3$–$C_6$-alkynyl, or is a $C_1$–$C_6$-alkyl, $C_3$–$C_6$-cycloalkyl, $C_2$–$C_6$-alkenyl or $C_3$–$C_6$-alkynyl which is mono- or polysubstituted by identical or different substituents from the group consisting of halogen, cyano, hydroxyl and $C_1$–$C_4$-alkoxy, or is a $C_2$–$C_8$-alkyl, $C_3$–$C_8$-cycloalkyl, $C_3$–$C_8$-cycloalkyl-$C_1$–$C_4$-alkyl, $C_2$–$C_8$-alkenyl or $C_3$–$C_8$-alkynyl which is interrupted once or more than once by oxygen, or is $C_1$–$C_4$-alkoxycarbonyl-$C_1$–$C_4$-alkyl which may optionally be substituted by halogen, or is $C_1$–$C_4$-alkoxycarbonyl-$C_2$–$C_4$-alkenyl which may optionally be substituted by halogen, or is the group $(CH_2)_p$—$NR^8R^9$, with the proviso that, if $R^{12}$ and $R^{31}$ are hydrogen or $R^{12}$ is hydrogen and $R^{31}$ is $C_1$–$C_4$-alkyl, $R^{13}$ may not be hydrogen or halogen, $R^{32}$ is hydrogen, $C_1$–$C_6$-alkyl, $C_3$–$C_6$-cycloalkyl, $C_2$–$C_6$-alkenyl, $C_3$–$C_6$-alkynyl, or is a $C_1$–$C_6$-alkyl, $C_3$–$C_6$-cycloalkyl, $C_2$–$C_6$-alkenyl or $C_3$–$C_6$-alkynyl which is mono- or polysubstituted by identical or different substituents from the group consisting of halogen, cyano, hydroxyl and $C_1$–$C_4$-alkoxy, or is a $C_2$–$C_8$-alkyl, $C_3$–$C_8$-cycloalkyl, $C_2$–$C_8$-alkenyl or $C_3$–$C_8$-alkynyl which is interrupted once or more than once by oxygen, or is $C_1$–$C_4$-alkoxycarbonyl-$C_1$–$C_4$-alkyl which may optionally be substituted by halogen, m is 3 or 4, n is 0, 1, 2 or 3, o is 1, 2 or 3, p is 2, 3 or 4 and X is oxygen or sulfur, with the proviso that when $R^6$ is

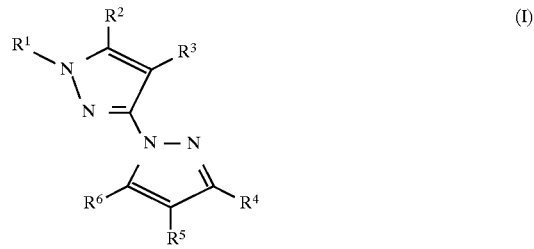

o is not 2 when $R^{32}$ is hydrogen or $C_1$–$C_6$ alkyl.

2. Substituted pyrazolylpyrazoles of the formula I, in which $R^1$ is methyl, $R^2$ is difluoromethoxy, $R^1$ and $R^2$ together form the group —$(CH_2)_4$—, $R^3$ is chlorine or bromine, $R^4$ is hydrogen, $R^5$ is nitro or cyano, $R^6$ is one of the groups

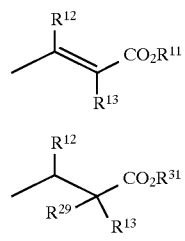

or

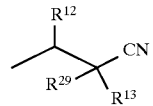

$R^{11}$ is $C_5$–$C_8$-alkyl, $C_3$–$C_6$-cycloalkyl, $C_2$–$C_6$-alkenyl, $C_3$–$C_6$-alkynyl, or is a $C_2$–$C_8$-alkyl, $C_3$–$C_8$-cycloalkyl, $C_3$–$C_8$-alkenyl or $C_3$–$C_8$-alkynyl which is interrupted once or more than once by oxygen, $R^{12}$ is hydrogen or methyl, $R^{13}$ is hydrogen or methyl, $R^{16}$ is hydrogen, $R^{17}$ is hydrogen, $R^{18}$, $R^{19}$, $R^{20}$, $R^{21}$, $R^{22}$, $R^{23}$, $R^{24}$ and $R^{25}$ independently of each other are hydrogen, halogen or $C_1$–$C_3$-alkyl, $R^{23}$ and $R^{25}$ together form a saturated 3-atom ring interrupted by an oxygen atom, $R^{29}$ is hydrogen or halogen, $R^{31}$ is hydrogen, $C_1$–$C_4$-alkyl, $C_5$–$C_8$-alkyl, $C_3$–$C_6$-cycloalkyl, $C_2$–$C_6$-alkenyl, $C_3$–$C_6$-alkynyl, or is a $C_1$–$C_6$-alkyl, $C_3$–$C_6$-cycloalkyl, $C_2$–$C_6$-alkenyl or $C_3$–$C_6$-alkynyl which is mono- or polysubstituted by identical or different substituents from the group consisting of halogen, cyano, hydroxyl and $C_1$–$C_4$-alkoxy, with the proviso that, if $R^{12}$ and $R^{31}$ are hydrogen or $R^{12}$ is hydrogen and $R^{31}$ is $C_1$–$C_4$-alkyl, $R^{13}$ may not be hydrogen, X is oxygen, and n is 0 and o is 1 or 2.

3. Herbicidally active composition which comprises at least one compound as claimed in claim 1.

4. Herbicidally active composition as claimed in claim 3 in the form of a mixture with carriers and/or auxiliaries.

5. A method for controlling monocotyledonous and dicotyledonous weed species in major agricultural crops which comprises treating the crops with a compound as defined in claim 1 or 2.

* * * * *

UNITED STATES PATENT AND TRADEMARK OFFICE
CERTIFICATE OF CORRECTION

PATENT NO. : 5,840,653
DATED : November 24, 1998
INVENTOR(S) : Michael Ganzer, et. al.

It is certified that error appears in the above-identified patent and that said Letters Patent is hereby corrected as shown below:

Column 34, line 12 "with the proviso that when $R^6$ is

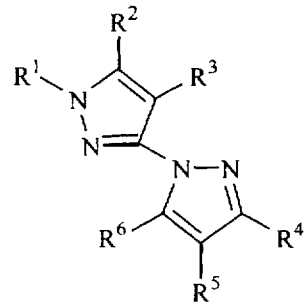

o is not 2 when $R^{32}$ is hydrogen or $C_1$-$C_6$ alkyl"

should read "with the proviso that when $R_6$ is -$(CH_2)_o$-A and when A is 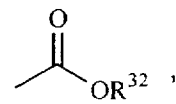

o is not 2 when $R^{32}$ is hydrogen or $C_1$-$C_6$ alkyl"

Signed and Sealed this

Fourth Day of April, 2000

Attest:

Q. TODD DICKINSON

Attesting Officer

Director of Patents and Trademarks